United States Patent [19]

Lebeault et al.

[11] Patent Number: 5,064,759
[45] Date of Patent: Nov. 12, 1991

[54] NOVEL BIOLOGICAL POLYMER

[75] Inventors: J. M. Lebeault, Villers-sur-Coudun, France; Jung-Hoe Kim; Joon-Ho Choi, both of Seoul, Rep. of Korea

[73] Assignee: Korea Advanced Institute of Science and Technology, Seoul, Rep. of Korea

[21] Appl. No.: 501,047

[22] Filed: Mar. 29, 1990

[30] Foreign Application Priority Data

Jun. 10, 1989 [KR] Rep. of Korea ............... 89-8029

[51] Int. Cl.$^5$ ................ C12P 19/04; C12N 1/20; C07H 1/00; C08B 37/00
[52] U.S. Cl. ................ 435/101; 435/252.1; 435/822; 536/1.1; 536/114; 536/123
[58] Field of Search .......... 435/101, 252.1, 822; 536/1.1, 114, 123

[56] References Cited

U.S. PATENT DOCUMENTS 4,477,655 10/1984 Holmes ........................... 524/9

OTHER PUBLICATIONS

Kor.J.Appl. Microbiol. Bioeng., vol. 17, No. 4, pp. 397–402 (Aug. 1989), Choi et al.: "New Extracellular Biopolymer Produced by Methylbacterium Organophilum from Methanol", Treatise reprinted from Proceedings of International Symposium on Screening of New Industrial Microorganisms and Products, Seoul, Korea (Oct. 27, 1989), Choi et al.: "Development of a New Biopolymer from Methanol as a Substrate".

Treatise reprinted from Proceedings of Asia-Pacific Biochemical Engineering Conference '90, Kyungju, Korea (Apr. 22-25, 1990) Kim et al.: "A Novel High Viscosity Polysaccharide-Biopolymer Produced from Methanol".

Primary Examiner—Johnnie R. Brown
Assistant Examiner—Pamela S. Webber
Attorney, Agent, or Firm—Oblon, Spivak, McClelland, Maier & Neustadt

[57] ABSTRACT

A new polysaccharide polymer and a process for producing the same are disclosed. The polysaccharide polymer as a biopolymer can be produced by culturing a heteropolysaccharide-producing strain of *Methylobacterium organophilum* on a aqueous culture medium containing methanol as a source of carbon and energy.

10 Claims, 4 Drawing Sheets

NOVEL BIOLOGICAL POLYMER

BACKGROUND OF THE INVENTION

1. Field of The Invention

The present invention relates to a process for the production of a new biological polymer and, more especially to a process for the preparation of a new biological polymer by a fermentation method using methanol as a source of carbon and energy.

The invention is also concerned with new biopolymers i.e., heteropolysaccharides falling within the category of biological polymers.

2. Description of The Prior Art

The polysaccharide which has been known is the xanthan gum produced by the fermentation of the genus Xanthomonas strain in a culture medium which generally utilizes carbohydrate such as glucose as a source of assimilable carbon. The xanthan gum has a high molecular weight of about $2 \times 10^6$ dalton, and consists of glucose, mannose and glucuronic acid. As a small amount of xanthan gum can exert a high viscosity, it may be useful as a viscosity control agent or a suspending agent for a solid-in-water and/or oil-in-water dispersion, and it may be applied in the secondary recovery of petroleum by water flooding (ACS Symposium Series No. 45, 144-160, 1977).

According to the fermentation method, the xanthan gum can be prepared by culturing *Xanthomonas campestris* on a culture medium (Adv. Appl. Microbiol., 23, 19-49, 1973) consisting of a 2-5% carbohydrate such as glucose and sucrose as a carbon and energy source and a 0.3% slurry from alcohol fermentation. The fermentation is carried out at pH 6.8 and at a temperature between 25° C. and 35° C., and the production with respect to a carbon source is then achieved in 50% and 70% yields. In aspects of economic consideration, however, the cost of carbon substrate such as carbohydrate is relatively high, and the development of a new fermentation system which can use other cheap carbon sources has been required.

SUMMARY OF THE INVENTION

It is an object of the present invention to provide a process for the production of a new heteropolysaccharide through the cultivation of a bacterium utilizing $C_1$-compounds which are over-produced at a low cost as an assimilable carbon source.

The new polysaccharide in accordance with the invention has the advantages that it is biologically degradable in nature, that it does not cause environmental pollution problem in use apart from the recalcitrant chemical synthetic polymer, and that it can be produced at a lower cost due to the use of an inexpensive carbon source, i.e., methanol. The polysaccharide functions as rheological control agents in food and petroleum chemical industry. It is also useful as gelling agents and water-absorbents for the absorption of a large quantity of moisture. According to the present invention, the method for producing a new biological polysaccharide through fermentation comprises culturing a facultative methylotroph of *Methylobacterium organophilum* or its mutants by classical mutation on a culture medium containing methanol as a source of carbon and energy.

The culture medium is maintained at a concentration between 0.2 and 1.0% by intermittent feeding of methanol and it is composed of nitrogen, phosphates, magnesium salts and trace elements. An ammonium salt, nitrate, or urea serves as an inorganic nitrogen source. Yeast extract, peptone, cornsteep liquor or casamino acid serves as an organic nitrogen source.

The minimal formulation of the medium was as follows: nitrogen source, 0.02-0.5%; phosphates 0.05-0.2%; magnesium salts, 0.04%; and trace elements such as calcium, manganese, molybdenum and copper, etc. Glucose, galactose, mannose, or succinic acid of about 0.5%, can stimulate the formation of the polysaccharide, and serves as a precursor. Fermentation is carried out at a pH between about 5 and 8, and at a temperature between 25° C. and 37° C. In order to maintain the dissolved oxygen at a level from 10 to 50% air saturation, the agitation speed is adjusted between 300 and 1000 rpm, and the aeration rate is within the range of 0.2 to 2.0 vvm.

Batch, two stage-, or fed-batch fermentations is carried out under the cultivation conditions previously described.

The crude, cell-free polysaccharide which is obtained through centrifugation is precipitated by an organic solvent such as acetone, ethanol and methanol from the fermentation broth. The precipitated polysaccharide is resolved in distilled water and dialyzed against the distilled water for desalting. After separation and purification, the pure polysaccharide is powdered by freezing-drying method.

BRIEF DESCRIPTION OF THE DRAWINGS

The invention will be illustrated below by means of the accompanying drawings, wherein.

To determine the chemical identity and the characteristics of the biopolymer so obtained, various tests were performed and gave the following results:

(1) By elemental analysis of the biopolymer, the composition is found to be composed of : carbon (C), 25-35%; nitrogen (N), 0.2-1.0%; hydrogen (H), 3-6%; oxygen (O), 35-50%; and ash, 5-30%.

Figure 1:
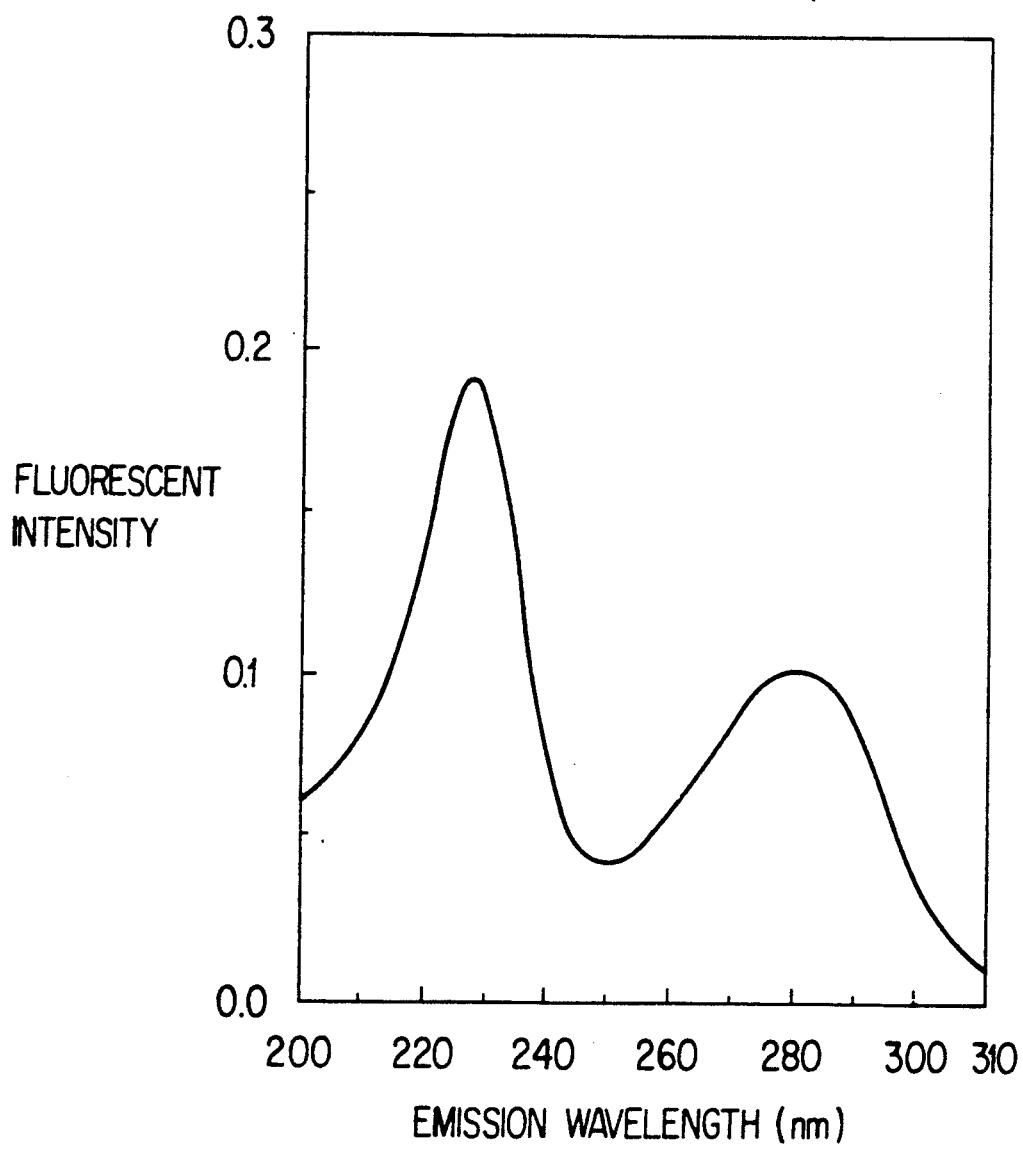
FIG. 1 shows a fluorescence spectrum of the polysaccharide in accordance with the invention.

(2) By running a UV spectrofluorescence, it is found that the polysaccharide contains protein but it does not contain nucleic acid since there were peaks at 280 nm. (FIG. 1).

Figure 2:
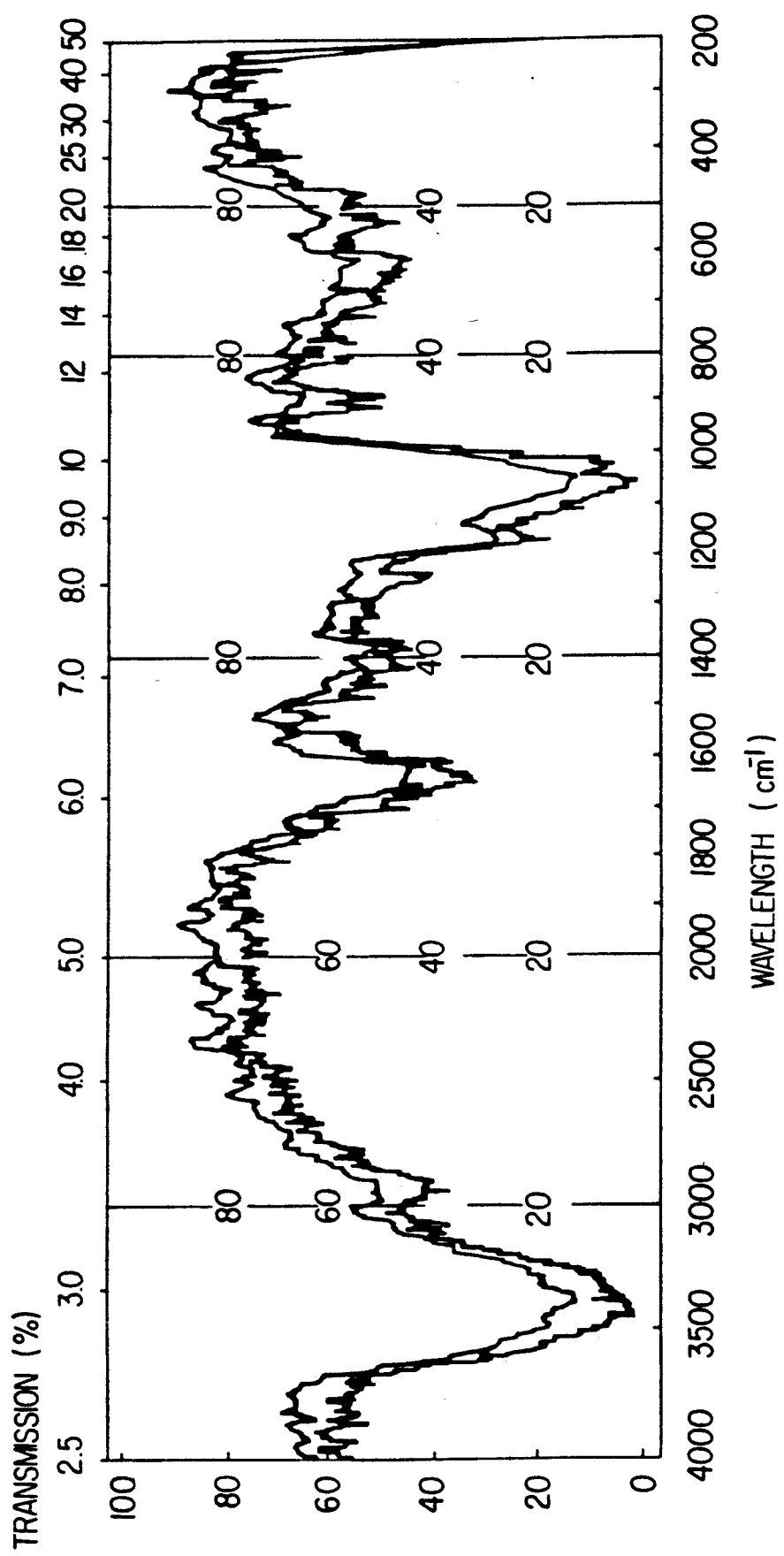
FIG. 2 shows a infra-red spectrum of the polysaccharide in accordance with the invention.

(3) An infra-red spectrum suggests the presence of amine groups (3400-3500 $cm^{-1}$), amino groups (1610-1655 $cm^{-1}$), and ketone groups (1710-1740 $cm^{-1}$; C=O, 1050-1090 $cm^{-1}$; C-O) (FIG. 2).

(4) The phenol-sulfuric method for total carbohydrate shows that the polymer contains 70-95% carbohydrate and the Lowry method for protein shows that the polymer contains 2-10% protein. The Friedemann method for pyruvic acid, the hydroxamic acid method for acetic acid, and the carbazole method for uronic acid indicate the content of organic acids of 5 to 15% (Pyruvic:acetic:uronic acid=4:1:8).

(5) After trifluoroacetic acid-hydrolysis, thin-layer chromatography, and HPLC analysis of the constituent sugar show the following results: glucose, 20-40%; galactose, 30-50%; and mannose, 20-35%.

(6) The test for polyhydroxybutyrate is negative (Okon Method Okon).

Figure 3:
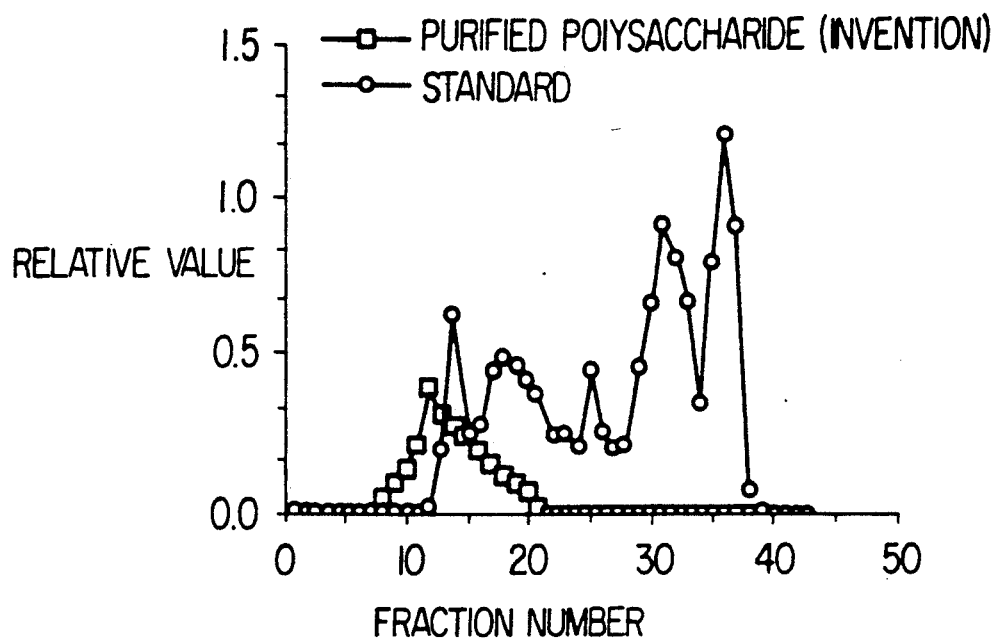
FIG. 3 shows elution profiles of the polysaccharide in accordance with the invention; and a standard sample (Blue Dextran) in gel permeation chromatography.
Figure 4:
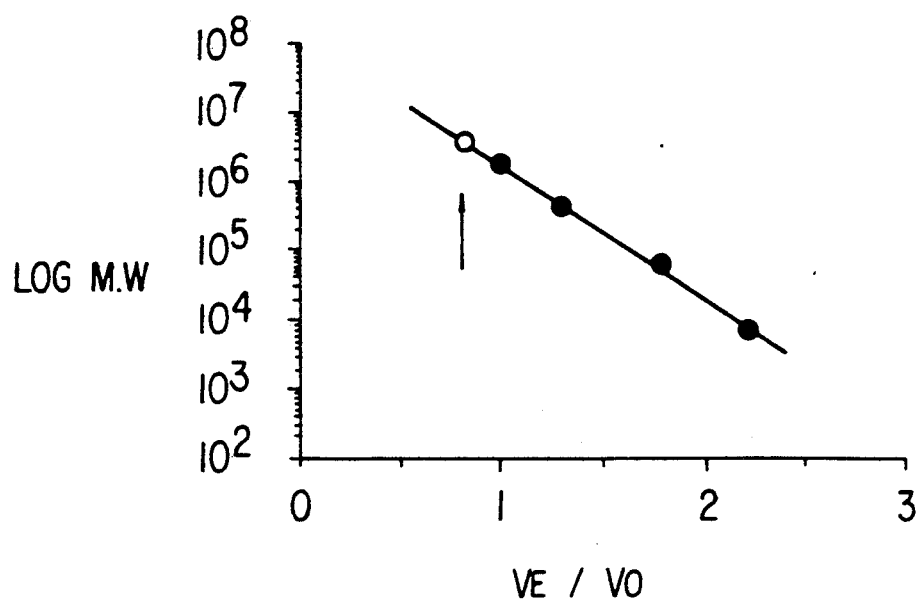
FIG. 4 shows a determination of the molecular weight of the polysaccharide in accordance with the invention; by means of gel permeation chromatography with Sepharose 6B.

(7) By gel permeation chromatography, the average molecular weight is determined to be between $2 \times 10^6$ and $6 \times 10^6$ dalton. (FIG. 3 and FIG. 4). The molecular weight of the new polysaccharide provided by the present invention is significantly higher than that of xanthan ($5-20 \times 10^5$) and pullulan ($1-5 \times 10^5$).

Figure 5:
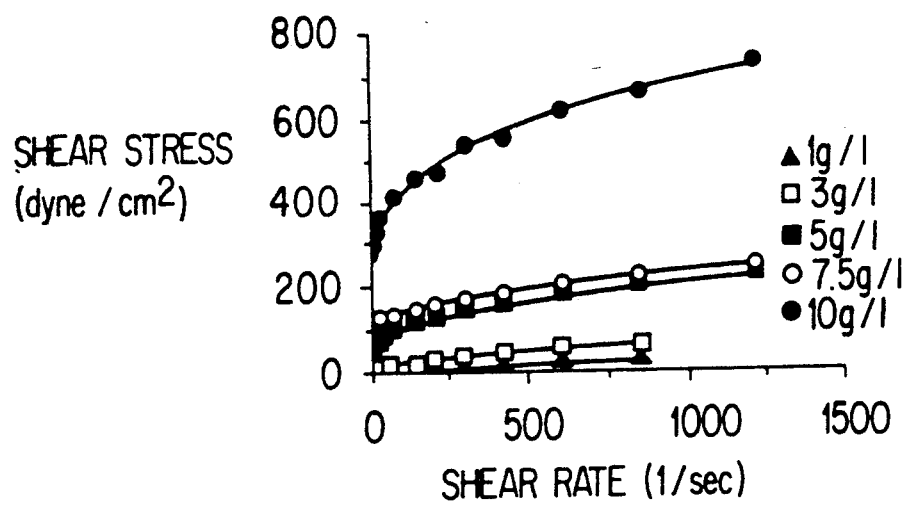
FIG. 5 shows rheograms of the various concentrations of the polysaccharide in accordance with the invention.
Figure 6:
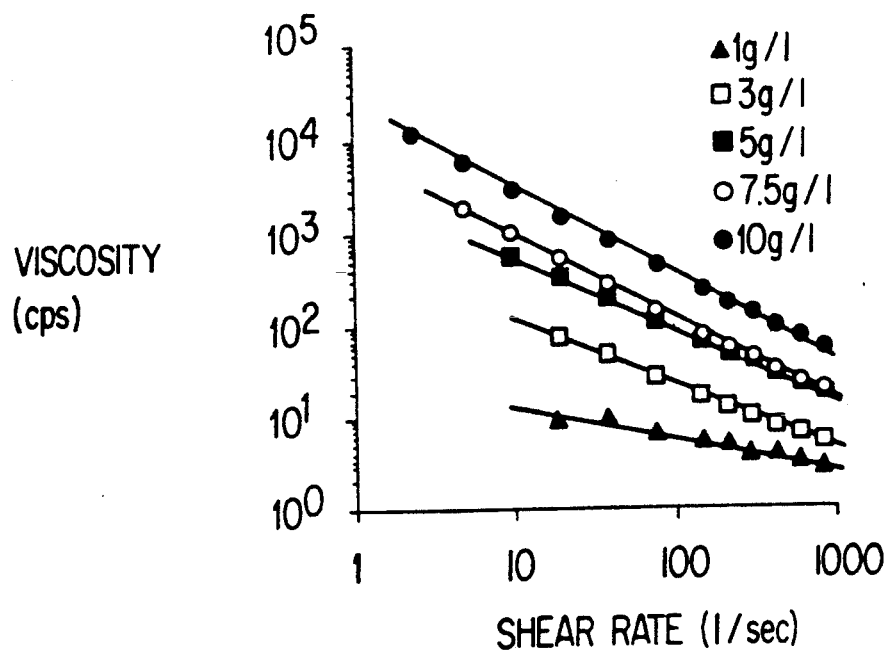
FIG. 6 shows a relationship between the viscosity and the shear rate at various concentrations of the polysaccharide in accordance with the invention.

(8) The rheological properties of the polysaccharide studied by measuring the viscosity of a solution of a polymer containing from 0.1 to 1 of (w/v) of the polysaccharide at 25° C. show the characteristics of pseudo-plastic non-Newtonian fluids. Its apparent viscosity sharply increases with the increase of its concentration (FIG. 5 and FIG. 6). For example, the apparent viscosity of 1% solution at the shear rate of 1 sec$^{-1}$ is about 18,000 cp. This is almost 10 times higher than that of xanthan gum and almost 200 times higher than that of pullulan.

(9) The viscosity of the polysaccharide solution remains stable at a pH ranging from 2 to 13 and at a temperature ranging from 20° C. to 60° C. The polysaccharide solution shows the characteristics of a near Newtonian fluid at the temperatures beyond 60° C.

(10) When adding monovalent or divalent metal ions to a new polysaccharide solution, a large amount of water is absorbed and a gel is formed. The addition of sodium chloride, for example, the polysaccharide solution formed a gel and absorbed water in range of 300 to 500 times at 1M NaCl.

In general, the biopolymers produced through fermentation by a microorganism cannot be named based on its molecular structure apart from common polymers or organic compounds. Such may be named by a combination of the genus name of the originating microorganism and a suffix "an". For example, "xanthan" was named by combining the word "xanth" from the genus name of *Xanthomonas campestris* and a suffix "an". However, "pullulan" was named by combining the word "pullul" from the species name of *Aureobasidium pullulans* with the suffix "an". According to the established practice, we have named the polysaccharide obtained in accordance with the present invention "methylan".

PREFFERED EMBODIMENTS OF THE INVENTION

The following non-limiting examples are given to illustrate the present invention in greater detail.

EXAMPLE 1

One liter of a culture broth of the following compositions was sterilized at 121° C. for 15 minutes.

| Composition | Amount |
|---|---|
| (NH$_4$)$_2$SO$_4$ | 0.3 g/l |
| KH$_2$PO$_4$ | 0.63 g/l |
| Na$_2$HPO$_4$ | 1.06 g/l |
| MgSO$_4$.7H$_2$O | 0.45 g/l |

| Composition | Amount |
|---|---|
| Ca$^{++}$, Fe$^{++}$, Mn$^{++}$, Zn$^{++}$, Cu$^{++}$, Mo$^{++}$ | 100 mg/l |

The above broth was mixed with 0.5% by volume of methanol, inoculated with a *Methylobacterium organophilum* strain, and cultivated while agitating at 600 rpm at 30° C. for 2 days. The pH was adjusted to 7.0 with 10% KOH, and the dissolved oxygen level was maintained at above 30% air saturation.

At the end of the fermentation, the culture broth was centrifuged to remove bacterial cells. Then, ethanol was added in an amount of 2 volumes per volume of the broth supernatant obtained. The ethanol-broth combination was mixed well and the resulting cell-free polymers were recovered. The polymers were drained, then washed twice with 75% (v/v) ethanol, and finally dried by a freezing-drying method. 0.6 Gram of ploymers in solid form was obtained. An analysis thereof is as follows:

Glucose: 18.7%
Galactose: 28.2%
Mannose: 18.5%
Protein: 4.8%
Organic acid: 10.0% (pyruvic acid: uronic acid: acetic acid=4:8:1)
Inorganic ash: 22.2% (K+10.39%; Na+7.34%; Mg$^{++}$0.305%; Ca$^{++}$0.016%; Zn$^{++}$0.0056%; Fe$^{++}$0.0034%; Mn$^{++}$0.0004%; Cu$^{++}$0.004%; PO$_4^{-3}$1.60%; other 2.54)

EXAMPLE 2

Example 1 was repeated using 1.0% by volume of methanol, 1.2 g/l of polysaccharide was obtained.

EXAMPLE 3

Example 2 was repeated with adding 5 g/l of glucose as a precursor, and 2.0 g/l of polysaccharide was obtained.

EXAMPLE 4

Example was repeated with adding 0.5 g/l of yeast extract as a nitrogen source, and 1.5 g/l of polysaccharide was obtained.

EXAMPLE 5

The cultivation of Example 1 was repeated, and the residual concentration of methanol was maintained below 0.5% by intermittently adding methanol to the culture. After the 3-4 days cultivation, 4.6 g/l of polysaccharide was produced.

EXAMPLE 6

Example 5 was repeated utilizing a concentrated inoculum at about 5 g/l of the cells, and the pH is adjusted to 7.0 with a 10% ammonia solution over 10-20 hours. This resulted in the production of 10 g/l of polysaccharide.

EXAMPLE 7

The continuous fermentation is carried out at a dilution rate of 0.1 hr$^{-1}$, when the cell concentration reached to 5-6 g/l in the procedure of Example 5. 3.0 G/l of polysaccharide was obtained after about 2 days.

While the present invention has been described hereinabove with reference to several specific embodiments thereof, it is readily apparent that minor modifications, variations and substitutions may be made to the process of preparing the polysaccharide according to the invention in order to direct the process to the following derivatives thereof: 1) acylated derivatives; 2) carboxymethyl derivatives; 3) methylated derivatives; 4) propylene glycol ester derivatives; 5) hydroxypropyl derivatives; and 6) cationic derivatives.

What is claimed is:

1. A heteropolysaccharide or a derivative thereof, which is identified by the following characteristics:

| | |
|---|---|
| Molecular weight: | 2-6 × 10$^6$ dalton |
| UV spectrum: | no nucleic acid 2-10% of protein (Lowry method) |
| Constituents: | carbohydrate (glucose, 20-40%; galactose, 30-50%; mannose, 20-35%); protein(2-10%); organic acid, 5-15% (pyruvic acid: uronic acid: acetic acid = 4:8:1); and ash, 5-30% |
| Consistency Index (K): | 15,000-20,000 cps for 1% solution |

2. The heteropolysaccharide of claim 1, wherein the derivative is in the form of acetyl, carboxymethyl, propylene glycol ester, cationic or hydroxypropyl derivates.

3. A process for producing heteropolysaccharides, comprising:

culturing a *Methylobacterium organophilum* strain or mutants thereof on a culture medium containing a carbon and energy source; a nitrogen source selected from the group consisting of ammonium salts, nitrates, urea, yeast extract, peptone and casamino acid; and phosphates, magnesium and other trace elements.

4. The process as defined in claim 3, wherein the medium is composed of a nitrogen source 0.02-0.5%; phosphates, 0.05-0.2%; magnesium, 0.045%; and trace elements, below 0.01%.

5. The process as defined in claim 3 or 4, wherein the carbon and energy source is methanol.

6. The process as defined in claim 3, wherein the methanol is intermittantly fed into the culture broth so as to be maintained at a concentration between 0.2 to 1.0%.

7. The process as defined claim 3, wherein the inoculation with 0.1-10 g/l of inoculum are performed under the following culture conditions: agitation speed of 300-1000 rpm; aeration rate of 0.2-2.0 vvm; pH of 5 to 8; temperature of 25° C. to 37° C.; the dissolved oxygen in a level of 10-50% air saturation; and the feeding rate of methanol of 0.05 to 0.5 g - methanol/g-cel$^{-hr}$, and the feeding rate of nitrogen (NH$_4$ equivalent) of 1 to 50 mg/g-cell$^{-hr}$.

8. The process as defined in claim 3 or 4, wherein the addition of a precursor selected from the group consisting of glucose, mannose, galactose and succinic acid is performed.

9. The process as defined in claim 8, wherein said precursor is maintained at a concentration of about 0.5%.

10. The process as defined in claim 3 or 4, wherein said heteropolysaccharide is further subjected to acetylation, carboxymethylation, methylation, propylene glycol esterification, hydroxypropylation, or cationation.

* * * * *